United States Patent [19]

Kauvar et al.

[11] Patent Number: 5,846,722
[45] Date of Patent: Dec. 8, 1998

[54] SYSTEM TO DETECT SMALL MOLECULE/ PEPTIDE INTERACTION

[75] Inventors: Lawrence M. Kauvar; Eugene W. Napolitano, both of San Francisco, Calif.

[73] Assignee: Terrapin Technologies, Inc.

[21] Appl. No.: 731,613

[22] Filed: Oct. 16, 1996

[51] Int. Cl.$^6$ .............................. C12Q 1/68; C12P 21/00; C07K 13/00; C07H 21/04
[52] U.S. Cl. ......................... 435/6; 435/69.7; 435/91.1; 530/350; 536/23.4; 536/24.1
[58] Field of Search ................... 435/69.1, 91.1, 435/254.2, 325, 6, 69.7; 530/350; 536/23.4, 24.1

[56] References Cited

U.S. PATENT DOCUMENTS

| | | |
|---|---|---|
| 5,283,173 | 2/1994 | Fields et al. . |
| 5,322,801 | 6/1994 | Kingston et al. . |
| 5,597,719 | 1/1997 | Freed et al. ............................. 435/194 |
| 5,610,015 | 3/1997 | Wickens et al. ............................. 435/6 |
| 5,637,463 | 6/1997 | Dalton et al. . |

FOREIGN PATENT DOCUMENTS

| | | |
|---|---|---|
| WO 94 10338 WO | 5/1994 | WIPO . |
| 9602561A1 | 2/1996 | WIPO ............................. C07H 21/04 |
| WO 97 31113 | 8/1997 | WIPO . |

OTHER PUBLICATIONS

Activation of the RAF–1 Kinase Cascade by Coumermycin–induced Dimerization, Farrar, M.A. et al., *Nature*, vol. 383, 1996, pp. 178–181.

A Protein Kinase Substrate Identified by the Two–Hybrid System, Yang, X et al., *Science*, vol. 257, 1992, pp. 680–682.

Germino et al.. Screening for in–vivo protein–protein interactions. PNAS (USA). vol. 90:933–937, Feb. 1993.

Gupta et. al.. Partial reversal of multidrug resistance in human breast cancer cells by a N–myristoylated protein kinase C–alpha pseudosubstrate peptide. J. Biol. Chem. vol. 271(4):2102–2111, Jan. 26, 1996.

Spenser, D.M. et al., "Controlling Signal Transduction with Synthetic Ligands" *Science* (1993) 262:1019–1024.

Ullman, A. et al. "Characterization by in vitro Complementation of a Peptide corresponding to an Operator–proximal Segment of the β–Galactosidase Structural Gene of *Escherichia coli*", *J Mol Biol* (1967) 24:339–343.

Farrar, M.A. et al., "Activation of the Raf–1 Kinase Cascade by Coumermyciniduced Dimerization" *Nature* (1996) 383:178–181.

A three–hybrid system for detecting small ligant–protein receptor interactions, Edward J. Licitra and Jun o. Liu, Center for Cancer Res. and Depts. of Biology and Chem., MIT, Proc. Nat'l. Acad. Sci. USA, vol. 93, pp. 12817–12821, Nov. 1996, Biochemistry.

Controlling protein association and subcellular localization with a synthetic ligand that induces heterodimerization of proteins, Peter J. Belshaw, Staffan N. Ho, Gerald R. Crabtree and Stuart L. Schreiber, Howard Hughes Medical Inst., Dept. of Chem. and Chemical Biology, Harvard U. Cambridge, MA.; Proc. Nat'l. Acad. Sci. USA, vol. 93. pp 4604–4607, May 1996, Chemistry.

*Primary Examiner*—James Ketter
*Assistant Examiner*—William Sandals
*Attorney, Agent, or Firm*—Morrison & Foerster LLP

[57] ABSTRACT

Improved methods for determining interactions between peptides or proteins and small molecules are disclosed. The invention methods can be used to screen libraries of either the small molecules or the proteins. In general, the methods comprise contacting an agent/ligand complex consisting essentially of an agent to be tested for binding to a target protein coupled to a ligand capable of binding a proteinaceous ligand-binding domain with a first fusion protein comprising said target protein and a first complementary portion of a segregable protein; and a second fusion protein comprising a proteinaceous ligand-binding domain and a second complementary portion of said segregable protein; and detecting whether the first complementary portion and second complementary portion are brought into proximity.

37 Claims, 2 Drawing Sheets

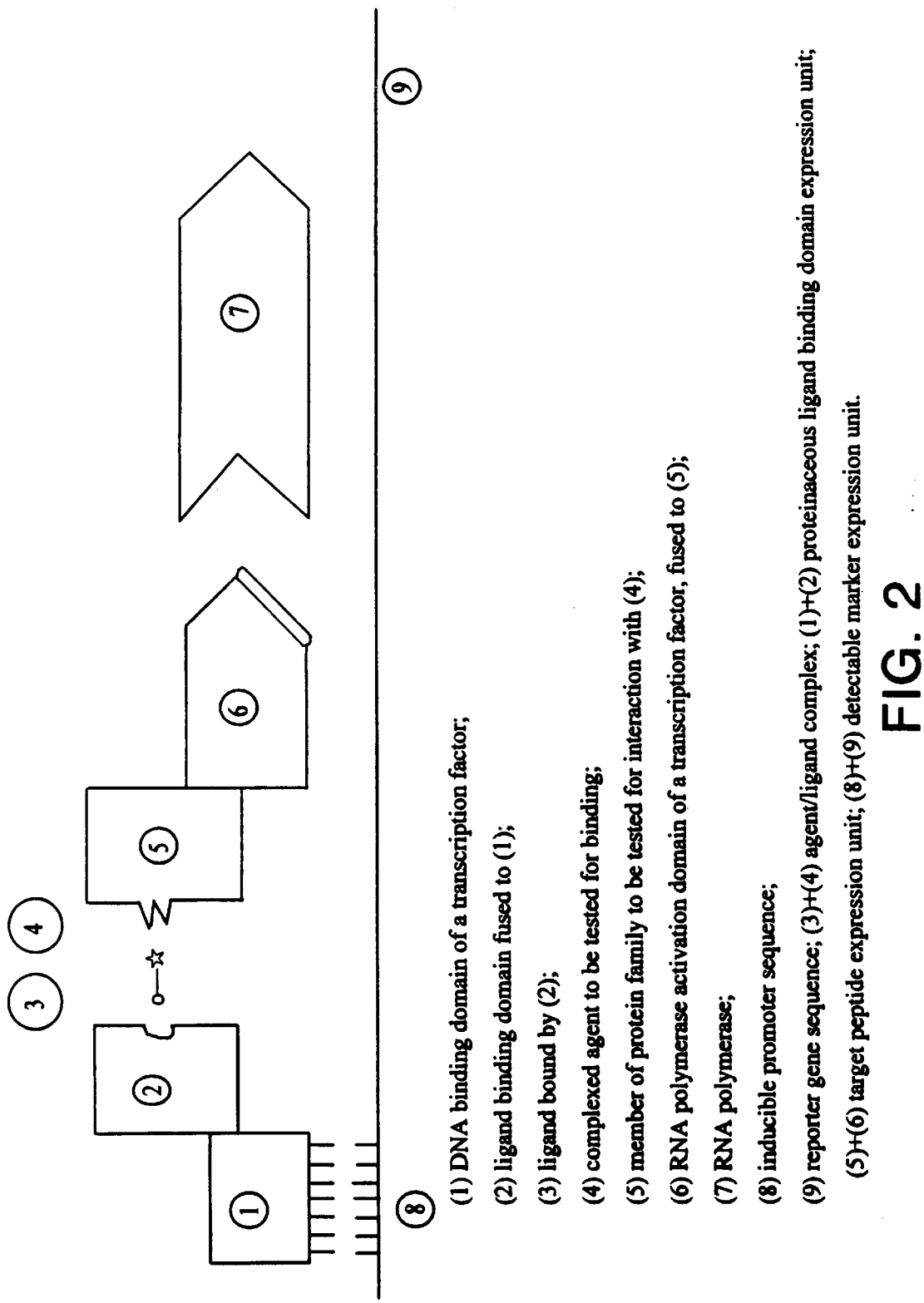

FIG. 2

(1) DNA binding domain of a transcription factor;
(2) ligand binding domain fused to (1);
(3) ligand bound by (2);
(4) complexed agent to be tested for binding;
(5) member of protein family to be tested for interaction with (4);
(6) RNA polymerase activation domain of a transcription factor, fused to (5);
(7) RNA polymerase;
(8) inducible promoter sequence;
(9) reporter gene sequence; (3)+(4) agent/ligand complex; (1)+(2) proteinaceous ligand binding domain expression unit;
(5)+(6) target peptide expression unit; (8)+(9) detectable marker expression unit.

SYSTEM TO DETECT SMALL MOLECULE/PEPTIDE INTERACTION

TECHNICAL FIELD

The application is in the field of pharmaceutical development. The present invention provides reagents, cells and methods for determining interactions between protein targets and small molecules, so as to identify unidentified target and related proteins, as well as to identify agents, particularly small molecules, that bind to an identified target protein.

BACKGROUND ART

A current focus of pharmaceutical development is the identification of agents (small molecules) which bind to a target protein and thus modulate a biological activity which is mediated by the target protein. However, few methods are available for identification of unknown target proteins that are bound by an agent with biological activity. Current technologies are generally based on directly determining whether an agent binds to a particular target protein or are based on determining whether the agent blocks a biological activity mediated by the target protein. Each of these current systems limits the number of agents and target proteins that can be effectively screened because of the nature and number of steps employed. Further, these methods typically focus on identifying the target in one species only. They do not provide a spectrum of viable targets whereby valuable information could be found concerning the nature of the interaction.

Recently, an assay system was described in which molecular genetic techniques are used to identify protein/protein binding events (Fields, et al., U.S. Pat. No. 5,283,173). The approach employed by Fields is a "two hybrid" protein system. In general, the Fields method uses two fusion proteins which are expressed within a single host cell, along with a reporter system to measure their interaction. The first fusion protein consists of one of the test proteins and a first portion of a transcription activator, e.g., a DNA binding domain. The second fusion protein consists of a second test protein and a second, complementary, portion of the transcription activator, e.g., an RNA polymerase activating domain. If the two test proteins bind to each other, the two transcription factor portions come into close proximity, thus reconstituting an active transcription factor, which then induces transcription of a gene encoding a detectable marker.

Although suitable for use in screening for protein/protein interactions, the system of Fields is not, in its current form, useable to screen non-protein agents, particularly small molecules, for binding to a single target protein, since Fields requires that both of the test substances whose binding is to be assessed be proteins capable of expression within a cell.

Fields represents a special case of a generic approach to detection of protein-protein interactions involving chimeric fusion proteins. Another representative embodiment of such approaches is found in the studies of dimerization of cytoplasmic domains of receptors by administration of small molecules as described by Spenser, D. M. et al., *Science* (1993) 262:1019–1024. In another embodiment, a chimeric construct of the Raf-1 serine/threonine kinase protein with a peptide sequence capable of dimerization in the presence of the antibiotic coumermycin is described by Farrar, M. A. et al., *Nature* (1996) in press. In addition to these cellular systems, it has been found that β-galactosidase can be segregated into complementary portions which become operable when placed in proximity by virtue of association in the tetrameric mature protein described by Ullman, A. et al., *J Mol Biol* (1967) 24:339–343.

For β-galactosidase, this is a result of "α- complementation" in which an inactive N-terminal deletion and an active point mutant can complement in the tetramer. It will be apparent that the reconstituted activated "protein" need not arise from a single amino acid chain; an additional example relates to the SH2 domain binding to a phosphotyrosine domain which constitute an active β complex that was never a single protein.

The present invention provides improvements to these techniques and adapts these systems for the interaction of agents other than protein, such as small molecules, with target proteins.

BACKGROUND ART

The invention provides a convenient system whereby libraries of target proteins can be screened for interaction with non-protein agents, whereby interaction profiles for proteins or small molecules can be obtained, and whereby libraries of small molecules can be screened for interaction with a target protein. In general, the invention provides a means to study the interaction of a target protein with a small molecule agent by utilizing two chimeric proteins —one comprising a first complementary proteinaceous portion of a segregable protein linked to a target protein and a second chimeric protein which comprises a second complementary portion of said segregable protein linked to a ligand-binding protein domain, where the activity of the segregable protein depends on proximity of the first and second complementary portions. The agent to be tested can then be supplied in a complex with a ligand capable of binding this ligand-binding domain. Thus the second chimeric protein will now be effectively associated with the agent to be tested. Successful interaction of the agent with the target protein results in proximity of the two complementary portions required for constituting the active protein or complex. The activity of the complex or protein can then be detected by means which depend on its nature. Also, depending on the nature of the active complex or protein, the assays can be conducted intracellularly or extracellularly.

In one preferred embodiment, the invention comprises an extension of the two-hybrid system of Fields described above wherein one of the test components is supplied in the form of a complex with a ligand, which ligand binds to a ligand-binding domain contained on one of the two fusion proteins in the two-hybrid system. By using this complex, binding agents other than proteins can be coopted to participate in the interaction which results in the reconstitution of the transcription factor required for production of the detectable marker in the two-hybrid system.

Thus, in this aspect, the invention is directed to a recombinant host cell modified to contain: i) a detectable marker expression unit which comprises an inducible promoter operably linked to a nucleotide sequence encoding a detectable marker, wherein the expression of said detectable marker is regulated by said inducible promoter; ii) a target peptide expression unit which comprises a nucleotide sequence encoding a fusion protein comprising a target peptide or protein and a first portion of a transcription activator protein selected from the group consisting of a DNA binding domain and an RNA polymerase activation domain; and iii) a ligand binding domain expression unit which comprises a nucleotide sequence encoding a fusion protein comprising a ligand binding domain and a second portion of a transcription activator protein selected from the group consisting of a DNA binding domain and an RNA polymerase activation domain, whichever is not employed in (ii).

The invention also employs other embodiments of the general theme of testing the ability of a target protein to bind to a small molecule agent by assessing a result of the proximity of two complementary portions of a segregable active protein which results from binding of agent to target. One additional embodiment involves taking advantage of the importance of dimerization or oligomerization of cytoplasmic regions of cellular surface receptors in transducing signals. If each partner in the dimer or oligomer can be brought into proximity, a signal will result which can then be detected using a suitable assay. Additional signaling events can occur by virtue of proximity of complementary portions or subunits of other proteins as well. Indeed, some systems can be practiced extracellularly, such as that based on the association of two segregable portions of β-galactosidase. In every instance, the invention method involves two fusion proteins, one comprising a first segregable portion of an active protein or complex and a target protein and the other fusion protein comprising a ligand-binding domain and the complementary portion of the segregable active protein or active complex. In all embodiments, the invention also employs a complex of an agent, typically a small molecule, covalently attached to a ligand, wherein the ligand binds to the ligand-binding domain. The complex is readily introduced into the cell, if required. The ligand secures the complex to the fusion protein containing the ligand-binding domain. In this way, a potential interaction between the agent and the target protein can be measured.

The invention is thus directed to methods to determine whether target proteins bind to agents, typically small molecules, and to methods to screen libraries of target peptides with respect to a biologically active agent, or to screen libraries of candidate small molecules with respect to a known target protein. The invention is also directed to methods to obtain profiles of a small molecule agent against a panel of target proteins or vice-versa. The method of the invention can also be used as a basis for a system of classifying proteins based on their binding specificities.

BRIEF DESCRIPTION OF THE DRAWINGS

FIG. 2 provides a detailed diagrammatic representation of one embodiment of the elements of the system of the present invention: (1) DNA binding domain of a transcription factor; (2) ligand binding domain fused to (1); (3) ligand bound by (2); (4) complexed agent to be tested for binding; (5) member of protein family to be tested for interaction with (4); (6) RNA polymerase activation domain of a transcription factor, fused to (5); (7) RNA polymerase; (8) inducible promoter sequence; (9) reporter gene sequence; (3)+(4) agent/ligand complex; (1)+(2) proteinaceous ligand binding domain expression unit; (5)+(6) target peptide expression unit; (8)+(9) detectable marker expression unit.

MODES FOR CARRYING OUT THE INVENTION

Figure 1A:
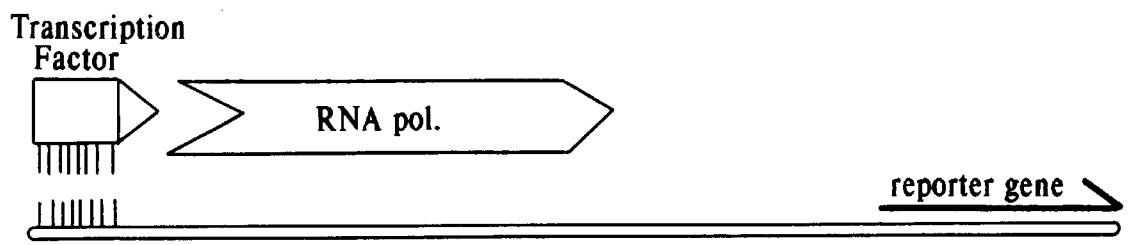
FIG. 1 provides a diagrammatic representation of an intact transcription factor regulating expression of a reporter gene (A), the Fields two hybrid protein system (B) and the invention hybrid system (C).

In detail, the present invention provides methods, reagents, and cells for use in determining whether an agent which is not necessarily a protein or peptide binds to a protein. Such methods, reagents, and cells can be used to screen a library of proteins to identify a protein bound by a particular agent or can be used to identify agents that bind a defined target peptide. The methods can also be used to provide profiles for various agents against panels of proteins using methods described in allowed U.S. Ser. No. 08/177,673 now U.S. Pat. No. 5587293 and Yang et al.,*Nucleic Acids Res* (1995) 23:1152–1156 incorporated herein by reference.

The detection of interaction of an agent with a target protein in every case relies on effecting a proximity of segregable complementary portions of a protein. By "segregable complementary portions of a protein" is meant that there are two proteinaceous segments which, when placed in proximity, are capable of effecting an activity, while when they are separated, the activity is not present. The proteinaceous complementary portions can originate from a single protein, as, for example, when they derive from a transcription activator, or may originate from related proteins as is the case described above for the β-galactosidase tetramer, or may be different proteins, such as an SH2 domain and a phosphotyrosine domain.

The interactions effected by the binding of target protein to a small molecule agent occur at the protein level, although the systems employed in the invention methods may be at the nucleic acid level which in turn effects generation of the fusion proteins. It is possible to conduct the assay entirely at the protein level, provided an extracellular system is employed. In such an in vitro system, fusion proteins, perhaps produced recombinantly, are used as simple reagents, the agent-containing complex is added, and the proximity of the portions of the segregable protein is assessed using an appropriate assay. This is illustrated by the use of fusion proteins containing complementary portions of β-galactosidase; when brought into proximity, the active enzyme can be detected by an appropriate enzyme activity assay. Thus, in such an in vitro system, a fusion protein containing one complementary portion of β-galactosidase is fused to a target protein; a second portion of the β-galactosidase is fused to a ligand-binding domain; and the agent to be tested, coupled with a ligand which binds to the ligand-binding domain is added to a reaction chamber containing the two fusion proteins. Successful binding of agent to target is detected by β-galactosidase activity.

More commonly, however, the method of the invention is conducted intracellularly and the fusion proteins are generated from recombinant materials introduced into the cell. The cell is also modified, if necessary, to provide a reporter system which will permit assessment of the proximity of the complementary portions of the segregable active protein. If the active protein is a transcription activator, generally the reporter system comprises a reporter gene operably linked to a promoter which is induced by the transcription factor. If the resultant of the interaction of the complementary portions of the active protein is generation of a signal, alternative assays can be used to detect the presence of the signal. The signal may itself result in transcription of an inducible gene either native to the cell or introduced. The effect need not be direct. For example, an interaction which stimulates production of a second messenger can lead to a detectable signal as a consequence of the signal transduction cascade induced by the second messenger. Further, the detectable signal does not necessarily require new gene transcription. For example, the generated signal may lead to translocation of an immunologically detectable protein from the interior of the cell to the surface.

This intracellular embodiment utilizes expression units for the fusion protein and, if needed, an expression unit for a reporter gene. The particulars of the intracellular embodiment can perhaps best be illustrated by a detailed description of the application of the yeast two-hybrid system to the invention method as follows.

Figure 1B:
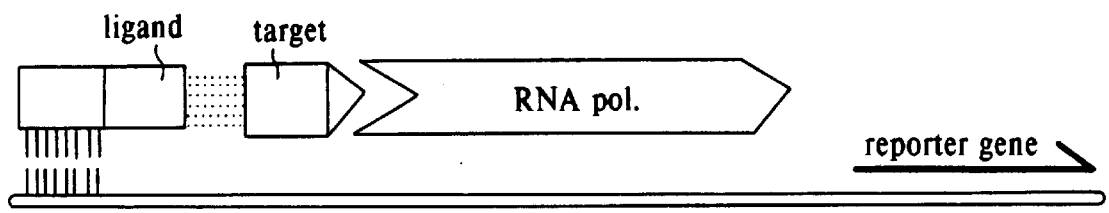
Figure 1C:
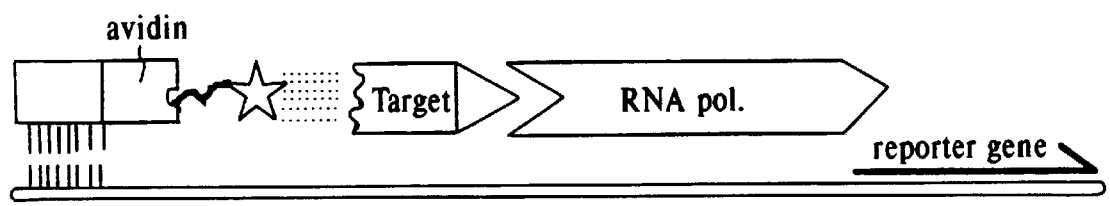
Figure 1C:
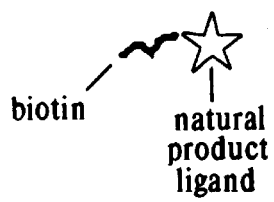

The two-hybrid method for detecting protein-protein interaction is disclosed by Fields et al. U.S. Pat. No. 5,283,173 (incorporated herein by reference). Specifically, the Field system provides plasmids that express two fusion (or hybrid) proteins in a host cell. The first plasmid comprises a nucleotide sequence that encodes either the DNA-binding domain of a transcription activator or the RNA activation domain of a transcription activator fused to a first peptide encoding sequence and the second plasmid comprises a nucleotide sequence that encodes either the DNA-binding domain of a transcription activator protein or the RNA polymerase activation domain of the transcription activator (whichever is not present in the first plasmid) fused to a second peptide encoding sequence. A third expression unit in the same host contains one or more detectable markers whose expression is controlled by a promoter that is activated by the associated two transcription activator domains contained in the fusion proteins. Interaction of the first and second proteins encoded by the plasmids causes the DNA binding domain and the activation domain to become closely associated, thus reconstituting the functionality of the transcription activator protein allowing the detectable marker gene to be expressed. See also FIG. 1 and Bartel, P. L. et al., *Nature Genet* (1996) 12(1):72–77. This system has been used to study the interaction of short peptides with a target protein, yielding quantitative results proportional to the known affinity constants over a studied range of 10–100 $\mu$M (Yang, M. et al., *Nucl Acids Res* (1995) 23(7):1152–1156). It has also been applied to the extracellular domains of receptors, expressed intracellularly (Young, K. H. et al., PCT application WO 95/34646).

The system of Fields could theoretically be extended to small molecules by replacing one of the fusion proteins with a small molecule covalently attached either to the RNA polymerase activation domain or the DNA binding domain of the transcription activator protein. The resulting domain/small molecule fusion would then need to be introduced into a cell in order to test whether the small molecule interacts with a target or test peptide/protein. Since permeabilization of a cell to the protein transcription activator domain will be difficult, such a method is not generally workable; further, coupling the small molecule to a protein is less convenient than producing a fusion protein.

The present invention offers a more efficient solution for extending the two-hybrid system to the study of small molecule/peptide(protein) interactions and solves the problems that are associated with protein permeabilization. By taking advantage of the interaction of a ligand with a proteinaceous ligand binding domain contained in one of the fusion proteins, the molecule can be introduced into the cell as part of a complex with a simple ligand. The cell will more readily be permeable to such a complex. For example, the interaction of biotin with a biotin-binding domain such as that of avidin could be used.

The methods and cells of this embodiment use four elements, of which three are nucleic acids: 1) a target peptide expression unit; 2) a proteinaceous ligand binding domain expression unit; and 3) a detectable marker expression unit. The fourth element is an agent/ligand complex.

As used herein, a "expression unit" refers to a nucleic acid molecule that contains a coding nucleotide sequence that can be transcribed and translated in a host cell. Expression units are comprised of an expression control element, for example, an inducible or constitutive promoter, that is operably linked to a protein-encoding sequence. The choice of the expression control element will depend primarily on the host cell employed. A skilled artisan can readily employ any art-known expression control sequence for use in the expression units of the present invention.

In this embodiment, both the target peptide expression unit and the proteinaceous ligand-binding domain expression unit employ sequences encoding fusion proteins which contain complementary portions of a transcription activator protein. The transcription activator protein has at least two separable portions, each needing to be present to have an active transcription activator protein. The preferred transcription activator will have a DNA binding domain peptide and RNA polymerase activation domain peptide.

Transcription activator proteins that have separate DNA binding and activation domains are known in the art for organisms such as yeast and include, but are not limited to, the yeast Gal4, GNC4, ADR1, Hap1, Swi5, Ste12, Mcm1, Yap1, Ace1, Ppr1, Arg81, Lac9, Qalf, VP16, and LexA proteins, non-mammalian nuclear receptors, such as ecdysone, and mammalian nuclear receptors such as the estrogen, androgen, glucocorticoids, mineralocorticoids, retinoic acid and progesterone receptors. The choice of the transcription activator protein used will depend primarily on the host cell chosen. The preferred transcription activators will be active in yeast, the preferred being the yeast Ga4, GNC4 and ADR1 transcription activator proteins.

Thus, the "target peptide expression unit" will encode a fusion protein containing "target peptide" and one of the domains described above which is a portion of a transcription activator protein. As used herein, a "target peptide" can be any peptide or protein of two or more amino acids in length. The terms "peptide" and "protein" are used interchangeably in the present application and do not contain implications as to the length of the amino acid sequence. The target peptide may be a known peptide or protein of known biological function, or may be an isolated protein whose biological function is not known. The target protein may also be contained in a library of peptides of differing amino acid sequences. When the invention methods are used to identify peptides that bind to a particular agent, then the target peptide will preferably be contained in a mixture of peptides with differing amino acid sequences, as in an expression library or a combinatorial peptide library. When the method is used to identify agents that bind to a particular target peptide, the preferred target peptide is either the entire protein, such as a receptor or a fragment of the receptor that contains a particular domain, for example, a fragment that contains the active site of an enzyme.

The second element is an "proteinaceous ligand binding domain expression unit." As used herein, a "proteinaceous ligand binding domain expression unit," or "ligand binding domain expression unit", is defined as a nucleic acid molecule that comprises a nucleotide sequence that encodes a fusion protein. The fusion protein contains "proteinaceous ligand binding domain" and a second portion of a transcription activator protein, either the RNA polymerase activation domain or the DNA binding domain, whichever is not encoded in the target peptide expression unit; namely if the target peptide expression unit contains a nucleotide sequence encoding the DNA binding domain, then the ligand binding domain expression unit will contain a nucleotide sequence encoding the RNA polymerase activation domain and vice-versa.

As used herein, a "proteinaceous ligand binding domain" is defined as a peptide that binds to a particular "ligand." As such, the "proteinaceous ligand binding domain" is a paired compound to the "ligand" employed. Examples of paired proteinaceous ligand binding domain and ligand compounds include, but are not limited to, a biotin binding domain/ biotin pair, the FLAG peptide detection system pair, an antibody/hapten pair, a carbohydrate binding lectin/ complementary carbohydrate pair, drug/protein pair (e.g., cyclosporine to cyclophilin or FK506 to FKBP) and single-chain Fv antibody fragment/agent ligand complex pair. The preferred pair is biotin binding domain/biotin. A skilled artisan can readily adapt any known proteinaceous binding domain/ligand pair for use in the present methods.

As used herein, a "biotin-binding domain" is defined as a peptide sequence that binds to biotin. The preferred biotin-binding domains are found in avidin and streptavidin (Hiller et al., *Biochem J* (1991) 278:573–585. Alternatively, biotin binding partners isolated from a random peptide library, such as those described by Saggio et al. *Biochem J* (1993) 293:613–616 or those identified using the present methods, can be used.

The third element is a "detectable marker expression unit." As used herein, a "detectable marker expression unit" comprises a nucleic acid molecule that encodes one or more detectable markers whose expression is controlled by a promoter that requires the binding of a transcription activator protein for transcription to occur. Promoters that require the binding of a transcription activator are well known in the art. These include, but are not limited to, the promoters bound by the yeast Ga 4, GNC4 and ADR1 proteins. The nucleotide sequence of the promoter employed will depend on the transcription activator protein chosen for the fusion proteins described above. The promoter is chosen such that transcription occurs when the two portions of the activator that are present in the fusion proteins become associated with each other and bind to the promoter.

As used herein, a nucleotide sequence is said to encode a detectable marker when, upon expression, the expressed nucleotide sequence produces a feature that can be detected. For example, 1) detection can be via complementation of nutritional auxotrophy, where the detectable marker complements a mutation found within the cell, such as a gene complementing a mutation in the biosynthetic pathways of amino acids, such as the His, Leu, Arg, Met, Lys and Trp pathways; 2) detection can be based on the production of an identifiable or assayable signal, such as β-galactosidase or green fluorescent protein (Atkins et al. *Curr Genet* (1995) 28:585–588); 3) detection can be by cell death, such as with the use of a toxic pro-drug; 4) detection can be based on the resistance to a normally toxic agent such as an antibiotic e.g., by the methods of Rotman U.S. Pat. No. 5,472,846; 5) detection can be based on genes conferring sensitivity to a chemical, such as the CYH2 or CAN1 protein; 6) detection can be based on the production of an agent that is readily detectable through assay means such as antibody binding or can readily be separated with a antibody or magnetically labeled probe; or 7) the reporter gene may provide a protein which migrates to the surface of the cell in which it is produced, permitting the separation of the cells expressing the reporter gene using affinity chromatography, for example, with respect to the cell surface reporter protein. A skilled artisan can readily adapt any one of the available detection/marker systems known in the art for use with the methods and cells of the present invention.

In one application of the present invention, the detection system is chosen such that cells can be screened based on the transient expression of the detection system employed. Such systems typically use a fluorescent marker protein, such as the green fluorescent protein, that can be identified without waiting for any significant cell growth to occur. A transient system employing a fluorescent marker allows the use of a fluorescent activated cell sorter that can identify a single fluorescent cell in a population of as many as $10^6$ cells.

The above three nucleic acid elements can be present as isolated nucleic acid molecules or can be present in one or more vectors. As used herein, "vector" is defined as a nucleic acid molecule that can autonomously replicate within a host cell. Vectors based on episomal elements such as plasmids, and vectors based on viral or chromosomal origins of replication, are well known in the art and can readily be modified to contain one or more of the nucleic acid elements used in the present invention. In one application, the three nucleic acid elements are contained on separate vectors. In another application, all of the elements are present on a single vector. In a third application, one or more of the elements are integrated into the chromosome of a host cell.

The fourth element used in the illustrated method is an "agent" that is typically other than a protein that has been covalently attached to a ligand to form an agent/ligand complex. The agent can be any substance, including peptides, small molecules, vitamin derivatives, and carbohydrates. The preferred agents are non-protein, small molecule agents. A skilled artisan can readily recognize that there is no limit as to the structural nature of the agents assayed by the present methods.

All of the invention embodiments utilize a ligand/agent complex. A variety of techniques known in the art can be used to attach a ligand to the agent. The method employed will depend primarily on the agent and ligand chosen. Such methods include, but are not limited to, direct chemical linking of the ligand to the agent or using a linker to attach the ligand to the test agent, such as the use of a photoactivated biotin sold by Pierce Chemical (Rockford, Ill). A skilled artisan can readily adapt any of the presently available methods for attaching a ligand, such as biotin, to agents for use in the present invention.

The elements described above are used in conjunction with a recombinant host cell that has been or can be transformed to contain the nucleic acid elements and the agent/ligand complex. As used herein, a "recombinant host cell" is defined as any cell that can be genetically altered so as to contain introduced nucleic acid molecules. The term "cell," "cells," "cell cultures," and the like are used interchangeably and can indicate a single cell or a plurality of cells as the context indicates. Both procaryotic and eucaryotic cells can be used; yeast cells are preferred, most preferably *Saccharomyces cerevisiae*.

Accordingly, embodiments conducted in intracellular environments provide cells transformed or modified to contain a ligand binding domain expression unit, and optionally a detectable marker expression unit as herein defined. Such cells will further be modified to contain a target peptide expression unit. The expression units contained in the hosts of this embodiment can be either integrated into the host chromosome or can be present within the host cell in the form of an episomal unit. A skilled artisan can readily use art-known methods to generate the host cells of the present invention.

To perform the method of the present invention, the test agent/ligand complex is introduced into a cell that contains a target peptide expression unit, a ligand-binding domain expression unit, and, if required, a detectable marker expression unit. A variety of techniques are presently known in the art for introducing small molecules and/or DNA into cells, and in particular yeast cells. Such methods include, but are not limited to, electroporation, lipofection, liposome delivery, transient saponification, natural uptake means, Penetratin-1 (a 16-amino-acid peptide known in the art as a cell permeation vehicle commercially available from Oncor (MD)), and chemical transformation, such as using lithium acetate.

The agent/ligand complex and expression vectors can be introduced into the host cell at the same time. Alternatively, one or more of the expression units can be introduced into the host cell prior to the introduction of the agent/ligand complex. In such an use, the expression units can further be integrated into the host chromosome or can be present as episomal units.

After the agent/ligand complex is introduced into the cell, the cell is incubated under conditions in which the target peptide expression unit and the ligand-binding domain expression unit are expressed. The agent/ligand complex will become associated with the ligand-binding domain expression unit due to the normal interaction of the ligand and the ligand-binding domain. If the agent and target peptide interact, the two portions of, for example, the transcription activator protein will come into close proximity, allowing the transcription activator protein to bind to the promoter of the detectable marker expression unit. If the agent/ligand complex does not bind to the target peptide, then the two portions of the transcription activator protein will not come into close proximity and the detectable marker expression unit will not be expressed.

The incubation conditions for the host cell will vary and will depend on the organism utilized, the detectable marker chosen, and the expression control elements (e.g. inducible or constitutive promoters) used in the target peptide expression unit and ligand binding domain expression unit. A skilled artisan can readily determine the appropriate conditions need to achieve expression of the target peptide expression unit and ligand-binding domain expression unit based on the specific elements employed.

One obstacle to the use of yeast as a host organism is that yeast possesses molecular pumps that are efficient in removing xenobiotics from within the cell. Some of this activity has been shown to be associated with a pump related to the mammalian MDR pump. Activity of this pump should be largely irrelevant in the present method because of the high affinity of most ligand binding domains for their cognate ligand. However, to increase the efficiency of the present method when yeast cells are used as a host cell, the yeast cells can contain a mutation that reduces the activity of the MDR pump. One such mutant presently known in the art is the sterile-6 mutant of *Saccharomyces cerevisiae*.

Although the foregoing description focuses on improvements in the two-hybrid system described by Fields, it will be apparent that the method of the invention is not limited to this embodiment. When the method of the invention is performed in an intracellular context, the cell used in the method will contain both a target peptide expression unit and a proteinaceous ligand-binding domain expression unit as defined in accord with the yeast two-hybrid system, except that the complementary portions of a segregable active protein or complex need not be portions of a transcription factor, but can be any two complementary portions which result in a detectable activity when brought into close proximity. Additional examples of such complementary portions have been described above. Depending on the cell used in the assay, it may or may not be necessary to include a separate detectable marker expression unit as defined above. The cell may inherently contain a mechanism for detecting the activity of the proximal protein components. Regardless of the choice for the complementary portions, however, the small molecule candidate binding agent will be supplied in the form of a complex with a ligand which has a strong affinity for the amino acid sequence that represents the ligand-binding domain. Thus, methods of the invention performed intracellularly involve cells that contain, at a minimum, expression units for the two relevant fusion proteins and optionally, when necessary, a detectable marker expression unit. The embodiments described above with respect to the nature of the ligand and ligand-binding domains, the types of markers possible, etc., are applicable in these embodiments as well.

The cells and methods of the invention are readily adapted for use in a 96-well plate format. Such a format allows for the screening of a large number of agents or target peptides, particularly the products of combinatorial enzymology, for example see McDaniel, et al., *Science* 262:1546–1550 (1993).

In one example of such a use, an agent that has a biological activity but whose protein target is unknown is used to identify the relevant target protein. In such an application, a peptide library comprised of a cDNA library, is used as the source for the peptide encoding sequences used in the target peptide expression unit. The collection of peptide encoding sequences thus results in a multiplicity of target peptide expression units. A population of host cells is transformed with the mixture such that each host cell, or a large proportion of the host cells, contain a different amino acid sequence for the target peptide.

An agent/ligand complex is then introduced into the transformed population of host cells. Host cells containing peptide sequences to which the agent binds can be detected via the detection system employed. If it is selected to use a fluorescent activated cell sorter and a fluorescent detection method, thousands of individual cells can be rapidly screened.

Cells identified as containing a peptide that binds the test agent are isolated and the nucleic acid encoding the target peptide examined using art-known DNA sequencing methods. The target peptide thus identified can then be 1) identified as the biological target of the agent, 2) used in a competitive binding format to identify other agents that may bind with greater/lesser selectivity, affinity, or avidity, to the target peptide, 3) used as a diagnostic agent for use in binding assays to determine the presence of the agent in a sample, or 4) used as an affinity ligand for the agent. The methods of the present invention are particularly useful in identifying diagnostic agents, such as glubodies (described in U.S. Ser. No. 08/380,188 incorporated herein by reference), that can be used in environmental monitoring, such as in assaying for the presence of a particular pesticide in a sample.

In addition to identifying a target receptor, information regarding the nature and sequences of peptides bound by a particular agent can be useful in assessing and predicting the toxicity of a given agent. Specifically, using a cDNA library as a source for the target peptide sequences, the method of the present invention will not only identify the biological target of a particular agent, but will also identify other molecules to which the agent binds. Such "runner-up" target peptides that are bound by the agent can be used to assess the toxicity and selectivity of a given agent.

In still another use, a known target, such as a receptor, can be used to screen a library of small molecules. Extensive libraries of compounds are available for testing or can be synthesized with the ligand incorporated, as in combinatorial chemistry methods; in this case, the ligand can be attached to all compounds as the first step of their synthesis, if desired. In this application, the host cell will contain, in the target peptide expression unit, a nucleotide sequence encoding the relevant receptor, and the agent/ligand complex will comprise a member of the candidate library covalently bound to the chosen ligand. The determination of the interaction of the agent with the target peptide is conducted as herein described. The agent/ligand complex can be supplied as part of a mixture of complexes containing a variety of agents, which can then be separated by dilution of the resultant transformed cells, or can be supplied as an individual member of a panel.

The reagents, cells and methods of the invention are also useful in obtaining profiles of agents against protein panels as described in allowed U.S. Ser. No. 08/177,673 now U.S. Pat. No. 5,587,293. In this use, a panel of cells containing the three expression units of the invention is provided, wherein each member of the panel contains a different target peptide expression unit. Each desired agent/ligand complex is then tested against each member of the panel to obtain the desired profile.

The following examples are intended to illustrate but not to limit the invention.

Preparation A

Preparation of Derivatized Agent

The agents to be tested for binding to protein are coupled to commercially available biotin analogs (Pierce Chemical) that incorporate a spacer arm optimized for use in affinity binding experiments and include various reactive groups. Such reactive groups may include a photoactivated free radical conjugating system, which yields a collection of conjugates with the biotin attached at different places. When this system is used at low stoichiometry, the probability that some of the conjugates will have the binding properties of the agent to be tested is high, and the relatively large size of most natural product agents makes them particularly suitable for this kind of derivatization. Alternatively, the reactive groups are less promiscuously reactive, based on known selectivities of certain radical generating moieties (Barton, D. H. et al., *J Am Chem Soc 61* (1961) 83:4083–4089), or widely used moieties such as N-hydroxysuccinimide for reaction with amines.

The biotin-derivatized agents are isolated on a commercially available avidin affinity sorbent (Sigma), and separated from free biotin by HPLC. Competitive binding assays confirm that the derivatized agents still bind the same site: following separation of bound and free agents by size exclusion filtration (Sarstadt centrifuge filtration devices), HPLC of the native agent determines the proportion bound to target in the presence of varying molar ratios of derivatized agent. The derivatized agent may also be analyzed by NMR and/or elemental analysis.

Preparation B

In Vitro Assay of Affinity Sorbent Containing Derivatized Agent

The derivatized agent is captured on commercially available agarose beads conjugated with avidin (Sigma) to obtain affinity sorbent for the target. The purified protein target of the agent is applied to the sorbent and the binding capacity for target is measured by comparing protein content of the material applied to the sorbent with that of the unretained material. As a control, the bound proteins can also be eluted under strongly denaturing conditions, separated by SDS gel electrophoresis, blotted to a membrane, and probed with commercially available antibodies specific for the known target proteins.

The specificity of an affinity sorbent is also evaluated by contacting it with tissue extracts known to contain the target proteins and eluting bound proteins. The eluted proteins are analyzed by electrophoresis followed by silver staining and/or by staining membrane-transferred material with appropriate antibodies.

The foregoing Preparations A and B describe methods for preparing materials for use in assessment of binding targets for agents to be tested and vice versa as well as for controls and for characterization of already identified interactions.

EXAMPLE 1

2-Hybrid Assay

A cDNA library in yeast is the source of fusion proteins comprising the DNA-binding domain of the yeast Gal4 transcription factor and the expression product of a cDNA insert. Vectors containing these inserts are prepared as described by Fields, et al. in U.S. Pat. No. 5,283,173 cited hereinabove. The biotin binding domain expression unit employs a minimal fragment of streptavidin with superior binding ability for biotin conjugates (Sano, T. et al., *J Biol Chem* (1995) 270(47):28204–28209).

The nucleotide sequence encoding the streptavidin fragment is ligated in reading frame with the RNA polymerase activating domain of Gal4 in the appropriate vector. The biotin-derivatized test agent of Preparation A is introduced into transiently permeabilized yeast cells containing the expression systems for cDNA encoding target and biotin binding domain and for the reporter gene β-galactosidase using the method of Gift, E. A. et al., *Biochem BiophysActa* (1995) 1234:52–62. Due to the high affinity of avidin for biotin, the test agents are well retained in the yeast cells. Expression of reporter is quantitated with the chromogenic substrate ONPG, O-dinitrophenyl-β-D-galactopyranoside (Sigma).

As controls, target protein expression systems employing sequences encoding proteins with known small molecule binding agents, for example cyclophilin or Protein Kinase C, are also included in the host yeast cell. As a further control, these vectors are spiked at decreasing doses into the cDNA library, and the recovery rate of the spiked clones indicates the noise level of the system.

An additional control is the sorbent binding assay described in preparation B.

Alternatively, the substrate for the determination of β-galactosidase levels generates a fluorescent product, in which case the assay for expression can be performed by a fluorescence-activated cell sorting (FACS). Similarly, the use of the fluorescent protein GFP (Cubitt, A. B. et al., *Trends Biochem Sci* (1995) 20:448–455) permits the use of FACS to assess expression.

We claim:

1. A method to determine whether an agent and a target protein interact, said method comprising the steps of:

contacting an agent/ligand complex comprising a small molecule agent to be tested for binding to a target protein coupled to a ligand that binds a proteinaceous ligand-binding domain with a first fusion protein comprising said target protein and a first complementary portion of a segregable protein; and a second fusion protein comprising a proteinaceous ligand-binding domain and a second complementary portion of said segregable protein; and detecting whether the first complementary portion and second complementary portion are brought into proximity.

2. The method of claim 1 wherein the first and second complementary portions of the segregable protein are subunits of a dimer of Raf-1 serine/threonine kinase.

3. The method of claim 1 wherein the first and second complementary portions of the segregable protein are the Raf-1 serine/threonine kinase and the cytoplasmic domain of the human interferon γ receptor ($H_\gamma R$).

4. The method of claim 1 wherein the first and second complementary portions of the segregable protein are portions of β-galactosidase.

5. The method of claim 1 wherein the first and second complementary portions of the segregable protein are portions of a transcription activator.

6. The method of claim 1 wherein the target protein is a known receptor and the agent is a member of a library of small molecules.

7. The method of claim 1 wherein the agent is a substance of known biological activity and the target protein is a member of a library of target proteins.

8. The method of claim 1 wherein the target protein is a member of a panel of target proteins.

9. The method of claim 1 wherein the first complementary portion and second complementary portion of the segregable protein are the cytoplasmic domains of a signaling receptor.

10. The method of claim 9 wherein the signaling receptor is a T lymphocyte antigen receptor.

11. A recombinant host cell in vitro modified to contain:
   i) a target protein expression unit which comprises a nucleotide sequence encoding a fusion protein comprising a target protein and a first complementary portion of a segregable active protein; and
   ii) a ligand binding domain expression unit which comprises a nucleotide sequence encoding a fusion protein comprising a ligand-binding domain and a second complementary portion of said segregable active protein which is modified to contain an agent/ligand complex comprising a small molecule agent to be tested for binding to said target protein coupled to a ligand which binds said proteinaceous ligand-binding domain.

12. The host cell of claim 11 wherein the first complementary portion and second complementary portion are cytoplasmic regions of a signaling receptor.

13. The host cell of claim 11 wherein said ligand is biotin and said ligand binding domain is a biotin binding peptide.

14. The host cell of claim 11, wherein the expression units (i) and (ii) and the agent/ligand complex are introduced into said host cell using a method selected from the group consisting of lipofection, eletroporation, and chemical transformation with lithium acetate.

15. The host cell of claim 11 wherein the expression of said target protein expression unit and said ligand-binding domain expression unit are controlled by constitutive promoters.

16. The host cell of claim 11 which is further modified to contain a detectable marker expression unit which comprises an inducible promoter operably linked to a nucleotide sequence encoding a detectable marker, wherein the expression of said detectable maker is regulated by said inducible promoter responsive to the association of said first and second complementary portions.

17. The host cell of claim 16 wherein the first and second complementary portions are portions of a transcription activator, one of said portions consisting of the DNA binding domain and the second portion consisting of the RNA polymerase activation domain.

18. The host cell of claim 17 wherein said detectable marker is selected from the group consisting of beta-galactosidase, a gene encoding a protein that complements a nutritional auxotrophy, green flourescent protein, and a selectable marker.

19. The host cell of claim 18 wherein said DNA binding domain and RNA polymerase activation domain are subunits of a protein selected from the group consisting of the Gal4, GCN4 and ADR1 proteins.

20. The host cell of claim 11 wherein said host cell is a yeast cell.

21. The host cell of claim 20 wherein said yeast cell contains a mutation that reduces the activity of the MDR pump.

22. The host cell of claim 21 wherein said mutation is the sterile-6 mutation.

23. A population of the host cells of claim 11 wherein said population comprises at least two host cells that express target proteins with different amino acid sequences.

24. The population of claim 23 wherein the target proteins are products of expression of a cDNA library.

25. A method to determine whether a small molecule agent and a target protein interact, said method comprising the steps of:
   a) incubating a recombinant host cell in vitro which contains
      i) a detectable marker expression unit which comprises an inducible promoter operably linked to a nucleotide sequence encoding a detectable marker, wherein the expression of said detectable maker is regulated by said inducible promoter;
      ii) a target protein expression unit which comprises a nucleotide sequence encoding a fusion protein comprising a target protein and a first portion of a transcription activator protein selected from the group consisting of a DNA binding domain and an RNA polymerase activation domain;
      iii) a ligand binding domain expression unit which comprises a nucleotide sequence encoding a fusion protein comprising a ligand binding domain and a second portion of a transcription activator protein selected from the group consisting of a DNA binding domain and an RNA polymerase activation domain, whichever is not employed in (ii); and
      iv) a small molecule agent/ligand complex wherein said ligand binds to said ligand-binding domain;
      under conditions in which said expression units (ii) and (iii) are expressed;
   b) detecting whether said detectable marker is expressed; and
   c) determining the level of binding of said agent to said target protein by the level of expression of said detectable marker.

26. The method of claim 25 wherein said ligand binding domain is a biotin binding domain and the ligand of said agent/ligand complex is biotin.

27. The method of claim 25 wherein said host cell is a yeast cell.

28. The method of claim 25 wherein the expression units and the test agent/ligand complex are introduced into said host cell using a method selected from the group consisting of lipofection, eletroporation and permeabilization using Penetratin-1.

29. The method of claim 25 wherein the expression units (a)(i), (a)(ii) and (a)(iii) are introduced into said host prior to the introduction of the agent/ligand complex (a)(iv).

30. The method of claim 25 wherein the expression of said target protein expression unit and said ligand-binding domain expression unit are controlled by constitutive promoters.

31. The method of claim 25 wherein said detectable marker is selected from the group consisting of beta-galactosidase, a gene encoding a protein which complements a nutritional auxotrophy, and a selectable marker.

32. The method of claim 25 wherein said DNA binding domain and said RNA polymerase activation domain are subunits of a protein selected from the group consisting of the Gal4, GCN4 and ADR1 proteins.

33. The method of claim 25 wherein the target peptide is a known receptor and the agent is a member of a library of small molecules.

34. The method of claim 25 wherein the agent is a substance of known biological activity and the target protein is a member of a library of target proteins.

35. The method of claim 25 wherein the target protein is a member of a panel of target proteins.

36. The method of claim 27 wherein said yeast contains a mutation that reduces the activity of the MDR pump.

37. The method of claim 31 wherein said mutation is the sterile-6 mutation.

* * * * *